US009984212B2

(12) United States Patent
Madabhushi et al.

(10) Patent No.: US 9,984,212 B2
(45) Date of Patent: May 29, 2018

(54) GROUP-SPARSE NONNEGATIVE SUPERVISED CANONICAL CORRELATION ANALYSIS (GNCCA)

(71) Applicant: Case Western Reserve University, Cleveland, OH (US)

(72) Inventors: Anant Madabhushi, Beachwood, OH (US); Haibo Wang, Cleveland Heights, OH (US)

(73) Assignee: Case Western Reserve University, Cleveland, OH (US)

( * ) Notice: Subject to any disclaimer, the term of this patent is extended or adjusted under 35 U.S.C. 154(b) by 419 days.

(21) Appl. No.: 14/612,317

(22) Filed: Feb. 3, 2015

(65) Prior Publication Data
US 2015/0254417 A1 Sep. 10, 2015

Related U.S. Application Data

(60) Provisional application No. 61/950,412, filed on Mar. 10, 2014.

(51) Int. Cl.
*G01N 33/48* (2006.01)
*G01N 33/50* (2006.01)
(Continued)

(52) U.S. Cl.
CPC ........ *G06F 19/3431* (2013.01); *A61B 5/7275* (2013.01); *G06K 9/0014* (2013.01); *G06K 9/00147* (2013.01); *G06K 9/6215* (2013.01); *G06K 9/6244* (2013.01); *G06T 7/0012* (2013.01); *A61B 5/055* (2013.01); *A61B 5/7264* (2013.01); *A61B 2576/00* (2013.01);
(Continued)

(58) Field of Classification Search
None
See application file for complete search history.

(56) References Cited

U.S. PATENT DOCUMENTS 6,542,249 B1 *  4/2003  Kofman ............. G01B 11/2513
                                                     356/601
2011/0161011 A1 *  6/2011  Hasson ................. A61B 5/055
                                                     702/19

OTHER PUBLICATIONS

Ginsburg, et al. "Variable Ranking with PCA: Finding Multiparametric MR Imaging Markers for Prostate Cancer Diagnosis and Grading." Prostate Cancer Imaging 2011, LNCS 6963, pp. 146-157, published Sep. 22, 2011.
(Continued)

Primary Examiner — Russell S Negin
(74) Attorney, Agent, or Firm — Eschweiler & Potashnik, LLC

(57) ABSTRACT

Methods, apparatus, application specific integrated circuits (ASIC)s and other embodiments associated with analyzing a cancerous prostate using group-sparse non-negative canonical correlation analysis (GNCCA) with a variable importance in the projections (VIP) score are described. One example apparatus includes a set of logics that acquires a set of features from a plurality of feature views of a region of tissue demonstrating cancerous pathology, produces a ranked set of discriminative features using GNCCA with the VIP score, optimizes computation of the GNCCA using a vector-block coordinate descent (BCD) approach, and provides a prostate cancer (CaP) grade or a biochemical recurrence (BcR) score based on the set of discriminative features. Embodiments of example apparatus may generate and display the CaP grade, BcR score, or set of discriminative features.

16 Claims, 13 Drawing Sheets

(51) Int. Cl.

| | |
|---|---|
| *G06F 19/00* | (2018.01) |
| *G06T 7/00* | (2017.01) |
| *A61B 5/00* | (2006.01) |
| *G06K 9/62* | (2006.01) |
| *G06K 9/00* | (2006.01) |
| *A61B 5/055* | (2006.01) |
| *G01R 33/56* | (2006.01) |

(52) U.S. Cl.
CPC .............. *G01R 33/5608* (2013.01); *G06T 2207/20081* (2013.01); *G06T 2207/30081* (2013.01)

(56) References Cited

OTHER PUBLICATIONS

Kim, et al. "Group Sparsity in Nonnegative Matrix Factorization." Proceedings of the 2012 SIAM International Conference on Data Mining, pp. 851-862, published Apr. 2012.

Singanamalli, et al. "Supervised Multi-View Canonical Correlation Analysis: Fused Multimodal Prediction of Disease Diagnosis and Prognosis." Medical Imaging 2014: Biomedical Applications in Molecular, Structural, and Functional Imaging, edited by Robert C. Molthen, John B. Weaver, Proc. of SPIE vol. 9038, 903805. Published Mar. 2014.

Peng, et al. "Feature Selection Based on Mutual Information: Criteria of Max-Dependency, Max-Relevance, and Min-Redundancy." IEEE Transactions on Pattern Analysis and Machine Intelligence, vol. 27, No. 8, Aug. 2005.

\* cited by examiner

610

710

810

910

GROUP-SPARSE NONNEGATIVE SUPERVISED CANONICAL CORRELATION ANALYSIS (GNCCA)

CROSS REFERENCE TO RELATED APPLICATIONS

This application claims the benefit of U.S. Provisional Application 61/950,412 filed Mar. 10, 2014.

BACKGROUND

The availability of multiple data streams allows the use of multimodal biomarkers to improve the performance of disease prognosis and diagnosis predictors. Discriminative features may be identified from multiple feature views acquired from different modalities. For example, patients likely to suffer prostate cancer (CaP) biochemical recurrence (BcR) may be identified using features acquired from a histology feature view and a proteomics feature view. Similarly, CaP grades may be predicted using features acquired from T2 weighted (T2w) magnetic resonance imaging (MRI) and dynamic contrast enhanced (DCE) MRI.

Multiple feature views increase the number of features from which discriminative features are selected. Selecting a useful set of discriminative features is a challenging problem. Some conventional methods of identifying discriminative features have employed canonical correlation analysis (CCA), while other conventional methods have used supervised multi-view (SMV) CCA. CCA addresses the problem of fusing features acquired from multiple modalities by finding a correlated metaspace that maximizes the signal, which is likely to be common to data from multiple feature views (e.g. modalities), while minimizing noise, which is more likely to be modality-specific.

Conventional methods that employ SMVCCA combine the principles of CCA with linear discriminant analysis (LDA) to find a subspace that maximizes the multi-view signal. SMVCCA also attempts to ensure the discriminability of provided class labels. While SMVCCA improves on CCA, both conventional methods are sub-optimal in practice when employed to select a useful set of discriminative features. Conventional correlation-based methods do not guarantee positive correlations of the selected features and often need a pre-feature selection step to reduce redundant features on each feature view.

Conventional SMVCCA is limited by latent components in the metaspace that can be negatively correlated. Negatively correlated features are less interpretable in clinical practice, and hurt the positive dependency between data and associated class labels. SMVCCA also requires a pre-feature selection step to reduce redundant features. The pre-feature selection step increases the time needed to select features and increases the complexity of conventional systems. SMVCCA also emphasizes the correlations of all modalities while neglecting modality-specific information. In some instances, a first modality may provide modality-specific information that is more useful than shared features. Conventional methods may ignore such useful modality-specific information due to a bias towards the modality with the greater number of features.

Conventional CCA methods have been modified to use a sparse non-negative approach. However, sparse non-negative CCA frameworks can only calculate the projection of a single feature view at a time. Sparse non-negative CCA frameworks thus have no group sparsity, and are difficult to extend to multiple feature views. Conventional methods for selecting a set of discriminative features also either neglect view information or address only class separability with a group lasso, as described in Ye, J, Liu, J: *Sparse methods for biomedical data*, SIGKDD 14(1) (2012) 4-15.

BRIEF DESCRIPTION OF THE DRAWINGS

The accompanying drawings, which are incorporated in and constitute a part of the specification, illustrate various example apparatus, methods, and other example embodiments of various aspects of the invention. It will be appreciated that the illustrated element boundaries (e.g., boxes, groups of boxes, or other shapes) in the figures represent one example of the boundaries. One of ordinary skill in the art will appreciate that in some examples one element may be designed as multiple elements or that multiple elements may be designed as one element. In some examples, an element shown as an internal component of another element may be implemented as an external component and vice versa. Furthermore, elements may not be drawn to scale.

DETAILED DESCRIPTION

Figure 1:
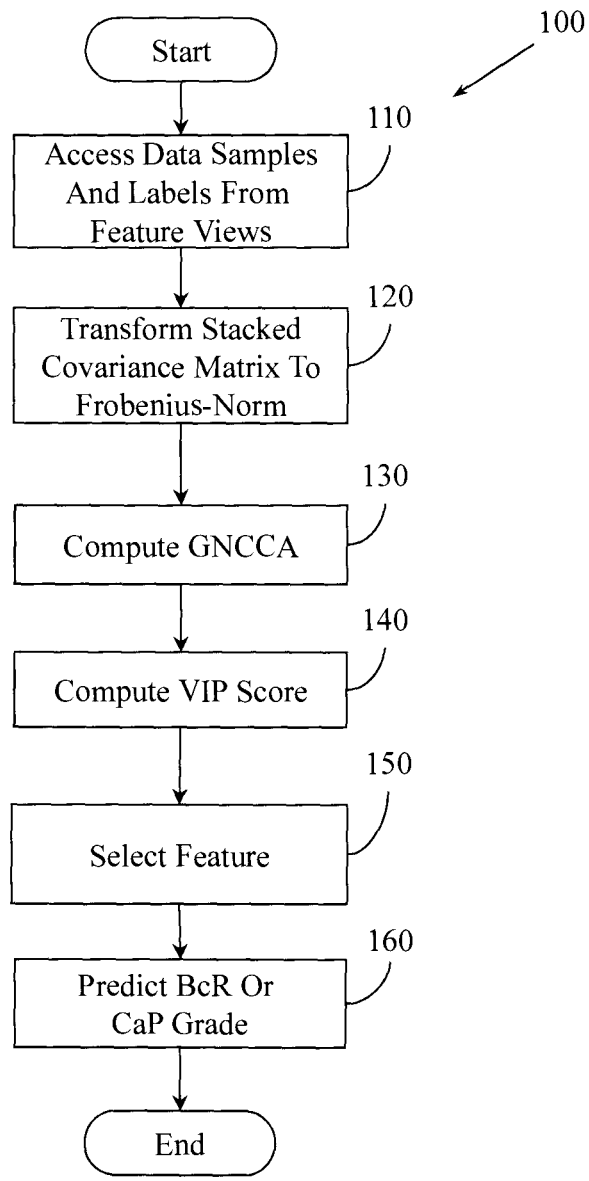
FIG. 1 illustrates an example method of predicting CaP BcR or CaP grade using GNCCA.

Example methods, apparatus, and application specific integrated circuits (ASICs) employ GNCCA and variable importance in the projections (VIP) to express the meaning of a reduced dimensional set of discriminative features to a human pathologist or other human user. Using VIP in conjunction with GNCCA allows the influence of the original, higher dimension set of features on the reduced dimension set to be discernible. Example methods, apparatus, and ASICs thus improve on conventional methods that lose or obscure the relationship between the higher dimensional set of features and the reduced dimensionality set of discriminative features. While examples are presented in the context of prostate cancer, example ASICs, apparatus, and methods may be applied to other similar appearing pathologies for other diseases.

Multiple data streams provide the opportunity to employ multimodal biomarkers for predicting disease diagnosis and prognosis. Conventional methods for selecting discriminative features include CCA and SMVCCA. CCA addresses the fusion of multimodal biomarkers by finding a correlated metaspace that maximizes the signal common to multiple modalities while minimizing noise that is modality-specific. SMVCCA combines CCA with LDA to find a subspace that maximizes multi-view signal while ensuring the discriminability of provided class labels. However, conventional correlation-based approaches do not guarantee positive correlations between selected features. Conventional approaches also often need a computationally expensive pre-feature selection step to reduce redundant features on each feature view.

While SMVCCA resolves some of the problems of CCA, SMVCCA has significant limitations in clinical practice. Latent components in the metaspace can be negatively correlated by SMVCCA, which is less interpretable in practice and negatively affects the positive dependency between data and their associated class labels. SMVCCA requires a pre-feature selection step to reduce redundant features, leading to increased complexity and running time, which is a detriment to clinical practice. Furthermore, SMVCCA emphasizes correlations of all modalities, but neglects modality-specific information, which leads to sub-optimal accuracy when grading CaP or predicting BcR. For example, SMVCCA may be biased towards a first modality that presents more features than a second, different modality that presents fewer features.

Example methods, apparatus, and ASICs improve on conventional methods for identifying discriminative features from multiple feature-views by incorporating a non-negativity constraint and a group-sparsity constraint. The non-negativity constraint guarantees positive correlations between features in the reduced representation space. The group-sparsity constraint enables simultaneous between-view feature selection and within-view feature selection. Example methods, apparatus, and ASICs thus emphasize correlations between feature views and class labels such that the selected features guarantee class separability.

Example methods, apparatus, and ASICs apply the non-negativity constraint onto both projection and coefficient factor matrices, ensuring that latent components are positively correlated. Example methods, apparatus, and ASICs employ the group sparsity constraint to enable simultaneous view association and within-view feature selection, thus capturing both view-shared and view-specific information. In particular, to encourage the association between feature views and class labels, example methods, apparatus, and ASICs keep the projection section of a label view non-sparse. Example methods, apparatus, and ASICs employing GNCCA thus improve on conventional methods that employ sparse nonnegative CCA by employing a more general matrix factorization scheme that allows updating view projections simultaneously.

Example methods, apparatus, and ASICs use a Variable Importance in the Projections (VIP) score with GNCCA to rank features. The VIP score enables selecting multi-modal features more accurately and efficiently than conventional methods. Example methods, apparatus, and ASICs using GNCCA-VIP more efficiently and more accurately interpret the importance of original features for feature-based classification tasks, including CaP grading and BcR prediction. GNCCA-VIP considers both view association and the discriminability of selected features.

Example methods, apparatus, and ASICs apply GNCCA-VIP to identify multimodal markers for different cancer prognosis tasks with greater accuracy and efficiency than conventional methods. Example methods, apparatus, and ASICs select the most clinically important features from extracted imaging and non-imaging features so that the extracted discriminative features may be used to predict CaP prognosis. For example, example methods, apparatus, and ASICs may identify CaP patients with and without 5-year BcR by fusing histological features and proteomic profiling values. Example methods, apparatus, and ASICs may predict CaP grades on a per-slice basis by fusing T2w MRI and DCE MRI image features. Example methods, apparatus, and ASICs may also localize CaP/non-CaP MRI voxels by fusing MRS and MRI image features.

Example methods, apparatus, and ASICs thus improve on conventional methods for multimodal feature selection by using a non-negativity constraint and a group sparsity constraint in a supervised CCA approach. The non-negativity constraint ensures that latent components are positively correlated. Group sparsity strengthens between-view sparsity and within-view sparsity allow for simultaneous view association and single-view feature selection. Example methods, apparatus, and ASICs achieve a more accurate classification result when identifying BcR than conventional methods including all-features, Fisher Score, T-test, mRMR, PCA-VIP, and SMVCCA-VIP. Example methods, apparatus, and ASICs out-perform conventional methods while selecting at least 2% of the total available features. In one embodiment, example methods, apparatus, and ASICs achieve a more accurate BcR prediction selecting 18 out of 892 features from multiple feature views. When selecting features from among textural features extracted from T2w MRI and kinetic features extracted from DCE MRI for predicting CaP grade, example methods, apparatus, and ASICs more accurately predict CaP grade while selecting only 2 out of 150 features across the different feature views. In another embodiment, example methods, apparatus, and ASICs select an average of 13 features out of 64 features obtained from MRS and MRI feature views when localizing CaP/non-CaP voxels. Example methods, apparatus, and ASICs increase the accuracy with which BcR and CaP grades are predicted, increase the accuracy of localizing CaP/non-CaP voxels, while reducing the number of features selected from multiple feature views. Example methods, apparatus, and ASICs maintain positive correlations among latent components and enable simultaneous view association and single-view feature selection. Example methods, apparatus, and ASICs therefore produce the concrete, real-world technical effect of increasing the probability that at-risk patients receive timely treatment tailored to the particular pathology presented. The additional technical effect of reducing the expenditure of resources and time on patients who are less likely to suffer recurrence or disease progression is also achieved. Example methods, apparatus, and ASICs thus improve on conventional methods in a measurable, clinically significant way.

Some portions of the detailed descriptions that follow are presented in terms of algorithms and symbolic representations of operations on data bits within a memory. These algorithmic descriptions and representations are used by those skilled in the art to convey the substance of their work to others. An algorithm, here and generally, is conceived to be a sequence of operations that produce a result. The operations may include physical manipulations of physical quantities. Usually, though not necessarily, the physical quantities take the form of electrical or magnetic signals capable of being stored, transferred, combined, compared, and otherwise manipulated in a logic, and so on. The physical manipulations create a concrete, tangible, useful, real-world result.

It has proven convenient at times, principally for reasons of common usage, to refer to these signals as bits, values, elements, symbols, characters, terms, numbers, and so on. It should be borne in mind, however, that these and similar terms are to be associated with the appropriate physical quantities and are merely convenient labels applied to these quantities. Unless specifically stated otherwise, it is appreciated that throughout the description, terms including processing, computing, calculating, determining, and so on, refer to actions and processes of a computer system, logic, processor, or similar electronic device that manipulates and transforms data represented as physical (electronic) quantities.

Example methods may be better appreciated with reference to flow diagrams. While for purposes of simplicity of explanation, the illustrated methodologies are shown and described as a series of blocks, it is to be appreciated that the methodologies are not limited by the order of the blocks, as some blocks can occur in different orders and/or concurrently with other blocks from that shown and described. Moreover, less than all the illustrated blocks may be required to implement an example methodology. Blocks may be combined or separated into multiple components. Furthermore, additional and/or alternative methodologies can employ additional, not illustrated blocks.

FIG. 1 illustrates a computerized method 100 for automatically analyzing a cancerous prostate using group-sparse non-negative supervised canonical correlation analysis (GNCCA) with a variable importance in the projections (VIP) score. GNCCA improves on conventional methods by introducing a group-sparsity penalty, relaxing the normalization constraint, and encouraging the relevance between features and class labels. Method 100 includes, at 110, acquiring a set of data samples X and a set of labels Y associated with the set of data samples X from a plurality of feature views K The plurality of feature views K includes a first set of features acquired from a first modality, and a second set of features acquired from a second, different modality.

Method 100 also includes, at 120, transforming trace ($W^T C_{xy} W$) to the Frobenius-Norm $\|Z-WH\|_F^2$. Transforming trace($W^T C_{xy} W$) to the Frobenius-Norm $\|Z-WH\|_F^2$ makes GNCCA solvable after integrating group sparsity. In one embodiment, C is a covariance matrix of K $C_{xy}$ denotes the stacking of the covariance matrix C and $YY^T$. $Z=[X^T Y^T]^T$ denotes the stacking of the n K-th view data samples X and the set of labels Y, where n is the number of data samples. In this embodiment, H is a coefficient matrix, and W is a basis matrix.

Method 100 also includes, at 130, computing the GNCCA. In one embodiment, GNCCA takes the form:

$$\min \frac{1}{2}\|Z - WH\|_F^2 + \alpha\|H\|_F^2 + \beta \sum_{k=1}^{K} \|W_k\|_{1,\infty},$$

$$\text{s.t. } \forall \; \|w_i^{(k)}\|^2 \leq = 1 - \beta, k = 1, \ldots ; i = 1, \ldots r;$$

$$\forall \; \|w_i^{(y)}\|^2 = 1 - \beta, i = 1, \ldots r;$$

$$H \geq 0, W \geq 0.$$

In this embodiment, $W \in \mathcal{R}^{m \times r}$, and $H \in \mathcal{R}^{r \times n}$. r is a dimension of reduced representation, where r<<m. $\|H\|_F^2$ is a first penalty term that allows GNCCA to avoid an arbitrarily large H. The relative influence of the first penalty term $\|H\|_F^2$ is controlled by $\alpha$. $\Sigma_{k=1}^K \|W_k\|_{1,\infty}$ is a second penalty term that constrains group sparsity. $\beta$ controls the relative influence of the second penalty term. K is the number of feature views. $\|\;\|_{1,\infty}$ represents $l_{1,\infty}$-norm. The non-negative constraints H≥0 and W≥0 ensure that both the canonical correlations of training and testing data are positive.

Example methods, apparatus, and ASICs improve on conventional approaches through the group-sparsity penalty on the K-view basis $W_{(1:K)}: \Sigma_{k=1}^K \|W_{(k)}\|_{1,\infty}$. The $l_{1,\infty}$-norm is defined by $\|W\|_{2,\infty} = \Sigma_{i=1}^r \|w_i\|_\infty = \|w_1\|_\infty + \ldots \|w_r\|_\infty$, which is the sum of vector $l_{1,\infty}$-norms of its columns. The $l_{1,\infty}$-norm is used to promote as many zero columns as possible in $W_{(1)}, \ldots W_{(K)}$, which has the effect that only the correlations of the non-zero feature views are maximized. GNCCA thus captures both the sharing of features among modalities and the uniqueness of each modality.

The condition $\|w_i^{(k)}\|^2 \leq 1-\beta$ ensures that the correlations are normalized. In particular, the relaxation $\forall \|w_i^{(k)}\|^2 \leq 1$ as used in conventional sparse nonnegative CCA is changed in example methods, apparatus, and ASICs to $\|w_i^{(k)}\|^2 \leq 1-\beta$ because the $l_{1,\infty}$ penalty is related to the constraints $\forall \|w_i^{(k)}\|^2 \leq 1$. As features become sparser, the $l_2$-norm of the features becomes smaller. Additionally, example methods, apparatus, and ASICs keep the normalization for the label-view basis $\forall \|w_i^{(y)}\|^2 \leq 1-\beta$, which ensures that the selected features are relevant with respect to the class labels.

Method 100 also includes, at 140, computing a VIP score $\pi_j$ for a feature j, where j is a member of K. The result of computing GNCCA leads to $$Z = \begin{bmatrix} X \\ Y \end{bmatrix} \approx \begin{bmatrix} W \\ W_y \end{bmatrix} H,$$

which leads to two approximate relationships: $X \approx WH$ and $Y^T \approx H^T W_y^T$. The first approximate relationship $X \approx WH$ introduces a lower feature representation H in W. The second approximate relationship $Y^T \approx H^T W_y^T$ models the lower feature representation H regressing to class labels $Y^T$. In this embodiment, W is a reduced feature space.

Computing the VIP score $\pi_j$ for the feature j includes computing $$\pi_j = \sqrt{\frac{m \sum_{i=1}^r \|w_y\|_2^i h_i h_i^T \left(\frac{w_{ji}}{\|w_i\|}\right)^2}{\sum_{i=1}^r \|w_y\|_2^i h_i h_i^T}}.$$

In this embodiment, $w_y^i \in W_y$ is a column entry of $W_y$. By employing VIP, example methods, apparatus, and ASICs can restore meaning to a reduced dimension set of discriminative features that otherwise would be de-coupled from the higher dimensional set of features. For example, an initial set of features may include 1000 features. Through principal component analysis (PCA), or other methods, the initial set may be reduced to a three dimensional set of features. However, the meaning associated with each of the 1000 features is lost through the PCA. Example methods, apparatus, and ASICs, through VIP, express the meaning of the reduced dimensional set of features to a human pathologist or other human user, so that the influence of the original initial set of features on the reduced dimension set is discernible. Example methods, apparatus, and ASICs thus improve on conventional methods that lose or obscure the relationship between the higher dimensional set of features and the reduced dimensionality set of features.

Method 100 also includes, at 150, selecting a feature based, at least in part, on the VIP score $\pi_j$ and the threshold $\sigma$. Selecting a feature based, at least in part, on the VIP score $\pi_j$ and the threshold $\sigma$ includes selecting a feature with a VIP score $\pi_j$ greater than or equal to $\pi \times \pi_{max}$. In one embodiment, $\pi_{max}$ is the largest VIP score. The threshold a is defined as $\sigma$: $0 < \sigma < 1$. The threshold a automatically determines the number of selected features.

In one embodiment, $\beta$, r, and $\sigma$ are determined using a Leave-M-Patient-out cross validation approach. In the Leave-M-Patient-out cross validation approach, M varies according to the number of patients in a data set. In this embodiment, $\alpha \|H\|_F^2$ is fixed at $0.1 \|H\|_F^2$. In other embodiments, $\beta$, r, and $\sigma$ may be determined using a different approach, and $\alpha \|H\|_F^2$ may be fixed at a different value. In still another embodiment, $\beta$, r, $\sigma$, and $\alpha \|H\|_F^2$ may vary.

Method 100 also includes, at 160, controlling an automated CaP analysis system to predict BcR or to predict a CaP grade. The BcR prediction or the CaP grade prediction are based, at least in part, on the selected feature. In one embodiment, the first set of features is a set of histological features extracted from a hematoxylin and eosin (H&E) stained histology section of a section of CaP tissue. The second set of features is a set of proteomic profiling values extracted from the H&E stained histology section. In another embodiment, the first set of features is a set of textural features extracted from a T2w MRI image of a section of CaP tissue. The second set of features is a set of kinetic features extracted from a DCE MRI image of the section of CaP tissue. T2 refers to spin-spin relaxation. In yet another embodiment, method 100, at 160, controls a CaP voxel localizing system to localize CaP and non-CaP voxels, based, at least in part, on the selected feature. In this embodiment, the first set of features is a set of magnetic resonance spectroscopy (MRS) features extracted from a voxel of an MRS image of a section of CaP tissue. The second set of features is a set of MRI features extracted from a voxel of an MRI image of the section of CaP tissue. In other embodiments, example methods, apparatus, and ASICs may acquire features from different modalities, different numbers of modalities, and may employ more than two sets of features.

Example methods, apparatus, and ASICs thus improve on conventional methods by using the non-negativity constraint to ensure that latent components are always positively correlated. Example methods, apparatus, and ASICs further improve on conventional methods by using group sparsity to strengthen both between-view and within-view sparsity, which allows for simultaneous view association and single-view feature selection. Example methods, apparatus, and ASICs also improve on conventional methods by ensuring that at least one feature is selected from each feature view. When applied to CaP prognosis prediction, example methods, apparatus, and ASICs identify discriminative feature subsets faster and with greater accuracy than conventional feature selection tools. Example apparatus and methods may also be applied to other diseases.

Identifying discriminative feature subsets with greater accuracy may lead to a more appropriately determined and applied treatment. Using a more appropriately determined and applied treatment may lead to less therapeutics being required for a patient or may lead to avoiding or delaying a biopsy, a resection, or other invasive procedure. When regions of cancerous or otherwise diseased tissue are more quickly and more accurately classified, patients with poorer prognoses may receive a higher proportion of scarce resources (e.g., therapeutics, physician time and attention, hospital beds) while those with better prognoses may be spared unnecessary treatment, which in turn spares unnecessary expenditures and resource consumption. Example methods, apparatus, and ASICs may thus have the real-world, quantifiable effect of improving patient outcomes.

While FIG. 1 illustrates various actions occurring in serial, it is to be appreciated that various actions illustrated in FIG. 1 could occur substantially in parallel. By way of illustration, a first process could access data samples and labels from a plurality of feature views, a second process could compute the GNCCA for the data samples and labels, and a third process could compute the VIP score for a selected feature. While three processes are described, it is to be appreciated that a greater or lesser number of processes could be employed and that lightweight processes, regular processes, threads, and other approaches could be employed.

Figure 2:
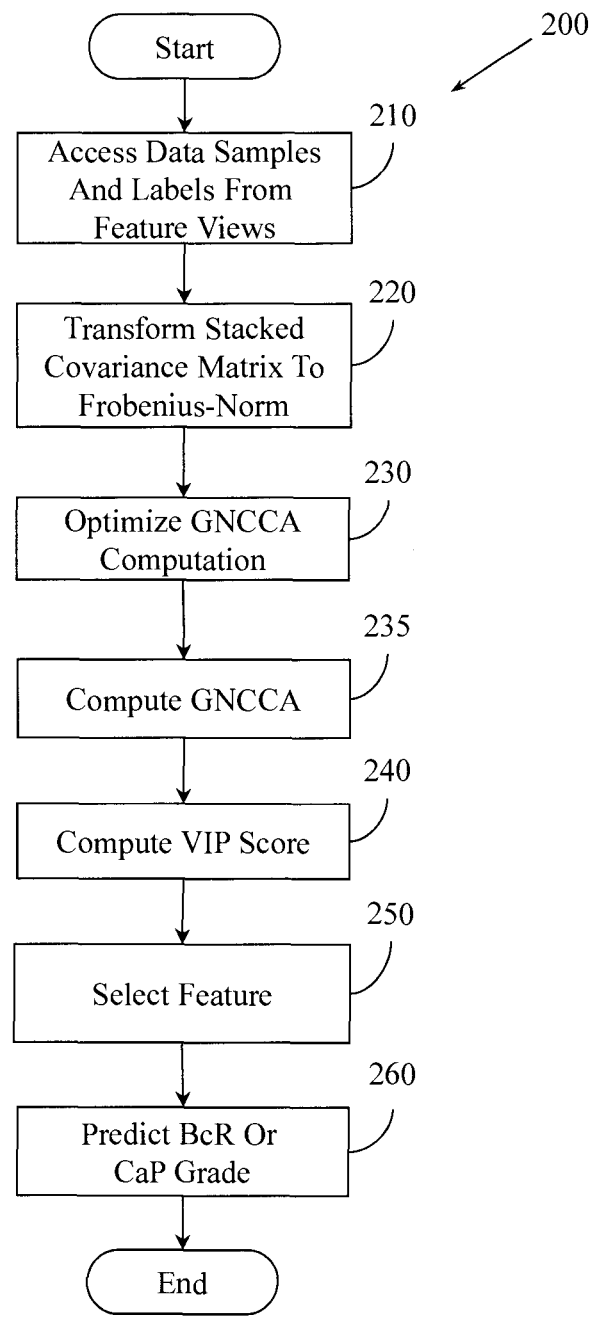
FIG. 2 illustrates an example method of predicting CaP BcR or CaP grade using GNCCA optimized with a vector-block coordinate descent approach.

FIG. 2 illustrates an example method 200 for automatically analyzing a cancerous prostate. Method 200 is similar to method 100, but method 200 includes the additional step 230 of optimizing the GNCCA computation. Method 200 includes, at 210, accessing a set of data samples and labels from a plurality of feature views. The plurality of feature views includes a first set of features acquired from a first modality, and a second set of features acquired from a second, different modality. The different modalities may include, for example, T2w MRI, DCE MRI, MRS, H&E stained histology sections, or proteomic profiling values. In different embodiments, more than two sets of features may be acquired from more than two different modalities. Method 200 also includes, at 220, transforming the stacked covariance matrix, the set of labels, and the transpose of the set of labels to the Frobenius-Norm.

Method 200 also includes, at 230, optimizing the computation of the GNCCA using a vector-block coordinate descent (BCD) approach. BCD updates one column of a factor matrix at each step while fixing all other values. In one embodiment, the GNCCA is described by $$\min \frac{1}{2} \|Z - WH\|_F^2 + \alpha \|H\|_F^2 + \beta \sum_{k=1}^{K} \|W_k\|_{1,\infty}.$$

In this embodiment, optimizing the GNCCA includes randomly initializing W and H, and then updating vectors of H, $W_{1:K}$, and $W_{(y)}$ in three steps until either the objective function is below a preset threshold or the maximum number of iterations has been reached.

In this embodiment, the first step of optimizing the GNCCA computation includes fixing W. Upon fixing W, method 200 updates a row vector $h_i \in \mathbb{R}^{1 \times n}$, $i=1, \ldots, r$ as $$h_i \leftarrow \underset{h \geq 0}{\arg\min} \frac{1}{2} \|R_i - w_i h\|_F^2 + \alpha \|h\|_2^2, \text{ where } R_i = Z - \sum_{j=1, j \neq i}^{r} w_j h_j.$$

In one embodiment, method 200 solves $$h_i \leftarrow \underset{h \geq 0}{\arg\min} \frac{1}{2}\|R_i - w_i h\|_F^2 + \alpha\|h\|_2^2$$

in a closed form as $$h_i \leftarrow \left[\frac{w_i^T R_i}{2\alpha + \|w_i\|^2}\right]_+.$$

In this embodiment, [ ]$_+$ denotes an element-wise projection to non-negative numbers.

The second step of optimizing the GNCCA computation includes fixing H and $W_{(y)}$. Upon fixing H and $W_{(y)}$, method 200 updates a column vector $w_i^{(k)}$, k=1, . . . , K. The column vector $w_i^{(k)}$, k=1, . . . , K is updated as $$w_i^{(k)} \leftarrow \arg\min_{w \geq 0, \|w\|^2 \leq 1-\beta} \frac{1}{2}\|R_i^{(k)} - w^{(k)} h_i\|_F^2 + \beta\|w^{(k)}\|_\infty.$$

In this embodiment, $R_i^{(k)} = Z^{(k)} - \sum_{j=1, j \neq i}^{r} w_j^{(k)} h_j$.

Updating the column vector $w_i^{(k)}$, k=1, . . . , K includes solving $$w_i^{(k)} \leftarrow \arg\min_{w \geq 0, \|w\|^2 \leq 1-\beta} \frac{1}{2}\|R_i^{(k)} - w^{(k)} h_i\|_F^2 + \beta\|w^{(k)}\|_\infty$$

by normalizing $w_i^{(k)}*$ s.t. $\|w_i^{(k)}*\| \leq 1-\beta$ and updating $w_i^{(k)}*$ as $$w_i^{(k)**} = \left[\frac{R_i^{(k)} h_i^{(T)}}{\|h_i\|^2}\right]_+ - w_i^{(k)*}.$$

In one embodiment, $w_i^{(k)}*$ is a solution to the problem described in Duchi, J., Shalev-Shwartz, S., Singer, Y., and Chandra, T., *Efficient projections onto the* 11-*ball for learning in high dimensions*. In: The 25th International Conference on Machine Learning (ICML). (2008) 272-279. In other embodiments, $w_i^{(k)}*$ may be obtained by different techniques.

The third step of optimizing the GNCCA computation includes fixing $W_{1:K}$ and H. Upon fixing $W_{1:K}$ and H, method 200 updates $W_{(y)}$ as $$w_i^{(y)} \leftarrow \arg\min_{w \geq 0, \|w\|^2 = 1-\beta} \frac{1}{2}\|R_i^{(y)} - w^{(y)} h_i\|_F^2.$$

In this embodiment, $R_i^{(y)} = Z^{(y)} - \sum_{j=1, j \neq i}^{r} w_j^{(y)} h_j$. In one embodiment, method 200, at 230, solves $$w_i^{(y)} \leftarrow \arg\min_{w \geq 0, \|w\|^2 = 1-\beta} \frac{1}{2}\|R_i^{(y)} - w^{(y)} h_i\|_F^2$$

by updating w as $$w_i^{(y)} \leftarrow \left[\frac{R_i^{(y)} h_i^{(T)}}{\|h_i\|^2}\right]_+.$$

Method 200 at 230 then normalizes $w_i^{(y)}$ by computing $$w_i^{(y)} \leftarrow \frac{w_i^{(y)}}{\|w_i^{(y)}\|} \sqrt{1-\beta}.$$

In other embodiments, optimizing the GNCCA computation may use more than three steps, and may use an approach different than the BCD approach.

Method 200 also includes, at 240, computing a VIP score for a feature. Method 200 also includes, at 250, selecting a feature based, at least in part, on the VIP score. Method 200 also includes, at 260 controlling an automated CaP analysis system to predict BcR or to predict CaP grade based, at least in part, on the selected feature.

In one example, a method may be implemented as computer executable instructions. Thus, in one example, a computer-readable storage medium may store computer executable instructions that if executed by a machine (e.g., computer) cause the machine to perform methods described or claimed herein including method 100, method 200, and method 300. While executable instructions associated with the listed methods are described as being stored on a computer-readable storage medium, it is to be appreciated that executable instructions associated with other example methods described or claimed herein may also be stored on a computer-readable storage medium. In different embodiments the example methods described herein may be triggered in different ways. In one embodiment, a method may be triggered manually by a user. In another example, a method may be triggered automatically.

Figure 3:
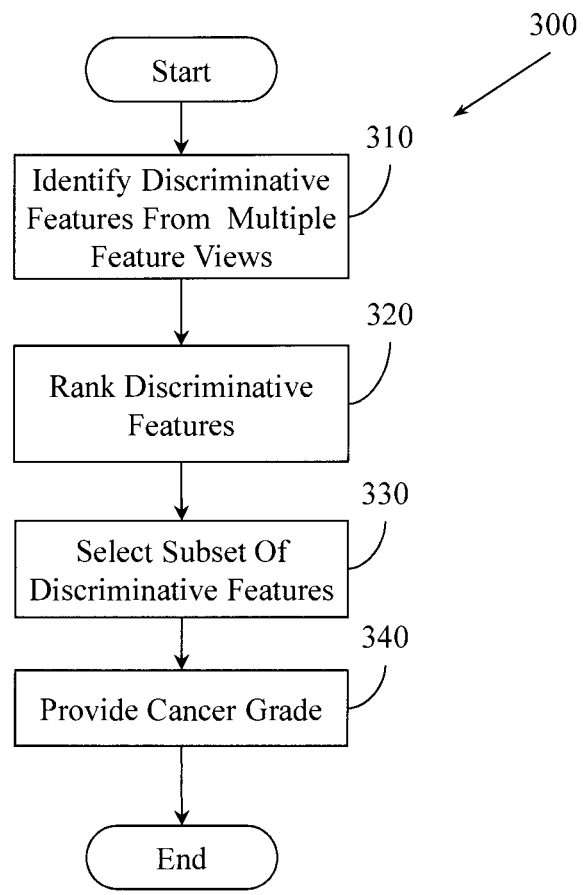
FIG. 3 illustrates an example method of predicting CaP BcR or CaP grade.

FIG. 3 illustrates an example method 300 for grading cancer or predicting cancer recurrence. While grading cancer and predicting cancer are described, example methods, apparatus, and ASICs may be more generally applied to other diseases. Method 300 includes, at 310 identifying discriminative features from multiple feature views. In one embodiment, method 300 uses GNCCA to identify discriminative features from the multiple feature views. In one embodiment, the multiple feature views may include features extracted from an H&E stained histology section, a set of proteomic profiling values extracted from the H&E stained histology section, a set of textural features extracted from a T2w MRI image, a set of dynamic features extracted from a DCE MRI image, a set of MRS features extracted from a voxel of an MRS image, or a set of MRI features extracted from a voxel of an MRI image. In another embodiment, the multiple feature views may include features extracted from other, different imaging modalities.

Method 300 also includes, at 320, ranking the discriminative features. In one embodiment, method 300 ranks the discriminative features using a VIP score. Method 300 also includes, at 330, selecting a subset of discriminative features. In one embodiment, selecting a subset of discriminative features is based, at least in part, on the VIP score and a threshold value. The number of selected features may be controlled by the threshold value. In one embodiment, the threshold value is greater than zero and less than one. The subset of discriminative features includes at least one feature obtained from a first feature view, and at least one feature obtained from a second, different feature view. For example, the first feature view may include at least 242 features acquired from an H&E stained histology section of a section of cancerous prostate, while the second feature view may include at least 650 features acquired from proteomic profiling values obtained from the H&E stained histology section. The first subset of discriminative features may include less than 18 features, and the second subset of discriminative features may also include less than 18 features. In other embodiments, other numbers of features may be acquired, and the first subset of discriminative features and second subset of discriminative features may include other numbers of discriminative features. In another embodiment, more than two subsets of discriminative features may be acquired from more than two feature views.

Method 300 also includes, at 340, providing a cancer grade or providing a cancer recurrence score. While a cancer grade and a cancer recurrence score are described, in other embodiments, other diagnostic or prognostic measures may be provided for other diseases. The cancer grade may be based, at least in part, on the subset of discriminative features. The cancer recurrence score may be based, at least in part, on the subset of discriminative features. In one embodiment, the cancer grade is a CaP grade. In another embodiment, the cancer recurrence score is a BcR score for CaP. In other embodiments, the cancer grade or cancer recurrence score may be associated with other types of cancer, including breast cancer, bone metastases, lung cancer, oral cancer, or testicular cancer. In other embodiments, values associated with prognostic tasks other than cancer grading and BcR scoring may be provided.

Figure 4:
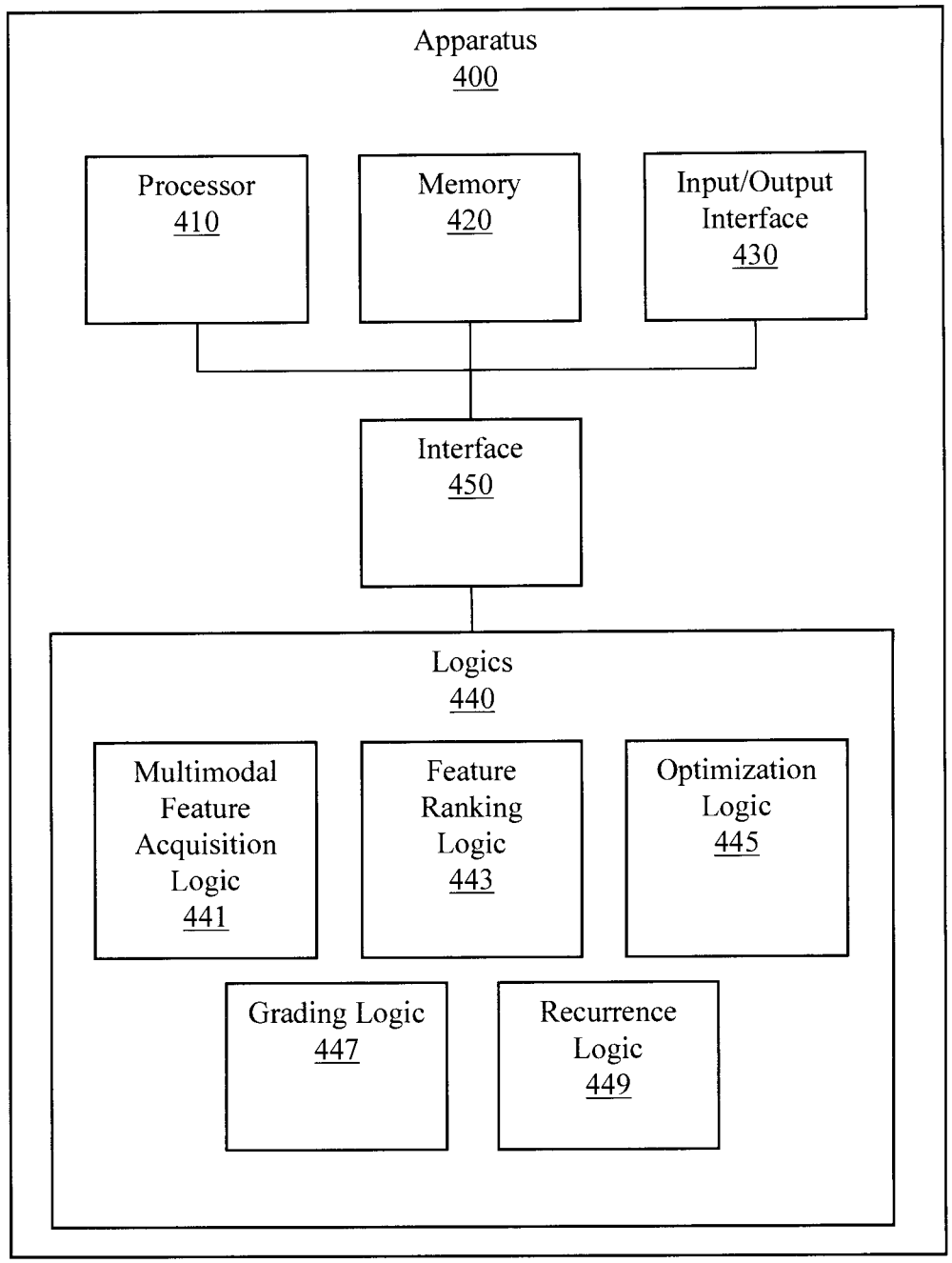
FIG. 4 illustrates an example apparatus that predicts CaP BcR or CaP grade.

FIG. 4 illustrates an example apparatus 400 that classifies a region of diseased tissue in an image. Apparatus 400 includes a processor 410, a memory 420, an input/output interface 430, a set of logics 440, and an interface 450 that connects the processor 410, the memory 420, the input/output interface 430, and the set of logics 440. The set of logics 440 includes a multimodal feature acquisition logic 441, a feature ranking logic 443, an optimization logic 445, a grading logic 447, and a recurrence logic 449. In one embodiment, the functionality associated with the set of logics 440 may be performed, at least in part, by hardware logic components. The hardware logic components may include but are not limited to, field-programmable gate arrays (FPGAs), application specific integrated circuits (ASICs), application specific standard products (ASSPs), system on a chip systems (SOCs), or complex programmable logic devices (CPLDs). In one embodiment, individual members of the set of logics 440 are implemented as ASICs or SOCs.

Multimodal feature acquisition logic 441 acquires a set of features from a plurality of feature views. The plurality of feature views may be acquired from an image of a region of diseased (e.g., cancerous) tissue. In one embodiment, the plurality of feature views includes a histological feature obtained from an H&E stained histology section, a textural feature, a structural feature, a proteomic profiling value, a T2w MRI image feature, a DCE MRI image feature, an MRS image feature, or an MRI image feature. In another embodiment, the plurality of feature views may include features obtained from other imaging modalities and from other non-imaging modalities.

Feature ranking logic 443 produces a ranked set of discriminative features from the set of features. Feature ranking logic 443 uses GNCCA and a VIP score to produce the ranked set of discriminative features. In one embodiment, feature ranking logic 443 uses a non-negativity constraint to ensure a positive correlation between members of a reduced representation subset of the set of features. Feature ranking logic 443 also employs a group-sparsity constraint to simultaneously select features from between feature views and from within feature views. Feature ranking logic 443 also uses the GNCCA to capture at least one shared feature across the plurality of feature views and at least one unique feature from a feature view.

Optimization logic 445 optimizes computation of the GNCCA. In one embodiment, optimization logic 445 uses a vector-block coordinate descent (BCD) method to optimize the GNCCA. The BCD method updates a column of a factor matrix at an iteration of a step while fixing other values. In one embodiment, optimization logic 445 randomly initializes a coefficient matrix and a basis matrix and then iteratively updates vectors in the coefficient matrix and the basis matrix until optimization logic 445 determines that either an objective function is below a preset threshold value, or a threshold number of iterations have been reached. The preset threshold value and the threshold number of iterations may be adjusted by a user. In one embodiment, optimization logic 445 uses a three-step approach to optimize the GNCCA. In a different embodiment, optimization logic 445 may use a different approach with a different number of steps to optimize the GNCCA.

Grading logic 447 produces a CaP grade based on the set of discriminative features produced by the feature ranking logic 443. Grading logic 447 may provide the CaP grade to a CADx system, to an automated cancer prognosis prediction system, to a human pathologist, or to another recipient. In another embodiment, grading logic 447 produces a grade associated with other types of cancer, including breast cancer, brain cancer, bone metastases, lung cancer, oral cancer, or testicular cancer. Grades for other diseases may be provided.

Recurrence logic 449 produces a recurrence score from the set of discriminative features produced by the feature ranking logic 443. Recurrence logic 449 may provide the recurrence score to a CADx system, to an automated cancer prognosis prediction system, to a human pathologist, or other recipient. In one embodiment, recurrence logic 449 predicts BcR for CaP. In another embodiment, recurrence logic 449 predicts BcR for other types of cancer, including breast cancer, brain cancer, bone metastases, lung cancer, oral cancer, or testicular cancer.

In one embodiment of apparatus 400, feature ranking logic 443, optimization logic 445, grading logic 447, and recurrence logic 449 are field-programmable gate arrays (FPGAs), application specific integrated circuits (ASICs), application specific standard products (ASSPs), system on a chip systems (SOCs), or complex programmable logic devices (CPLDs). In another embodiment, feature ranking logic 443, optimization logic 445, grading logic 447, and recurrence logic 449 may be other types of systems or circuits.

In one embodiment of apparatus 400, the set of logics 440 also includes a display logic. The display logic may control a CADx system to display the CaP grade or BcR score on a computer monitor, a smartphone display, a tablet display, or other displays. The display logic may control also control the CADx system to display the set of discriminative features. Displaying the CaP grade or BcR score may also include printing the CaP grade or BcR score. The display logic may also control the CADx to display an image of the region of tissue demonstrating cancerous pathology. The image of the region of tissue demonstrating cancerous pathology may include a representation of the CaP grade or BcR score for the image, as well as displaying the set of discriminative features. By displaying the CaP grade, the BcR score, the set of discriminative features, and the image of the region of cancerous tissue, example apparatus provide a timely and intuitive way for a human pathologist to more accurately predict prognoses for pathologies demonstrated by a patient, thus improving on conventional approaches for selecting discriminative features.

Figure 5:
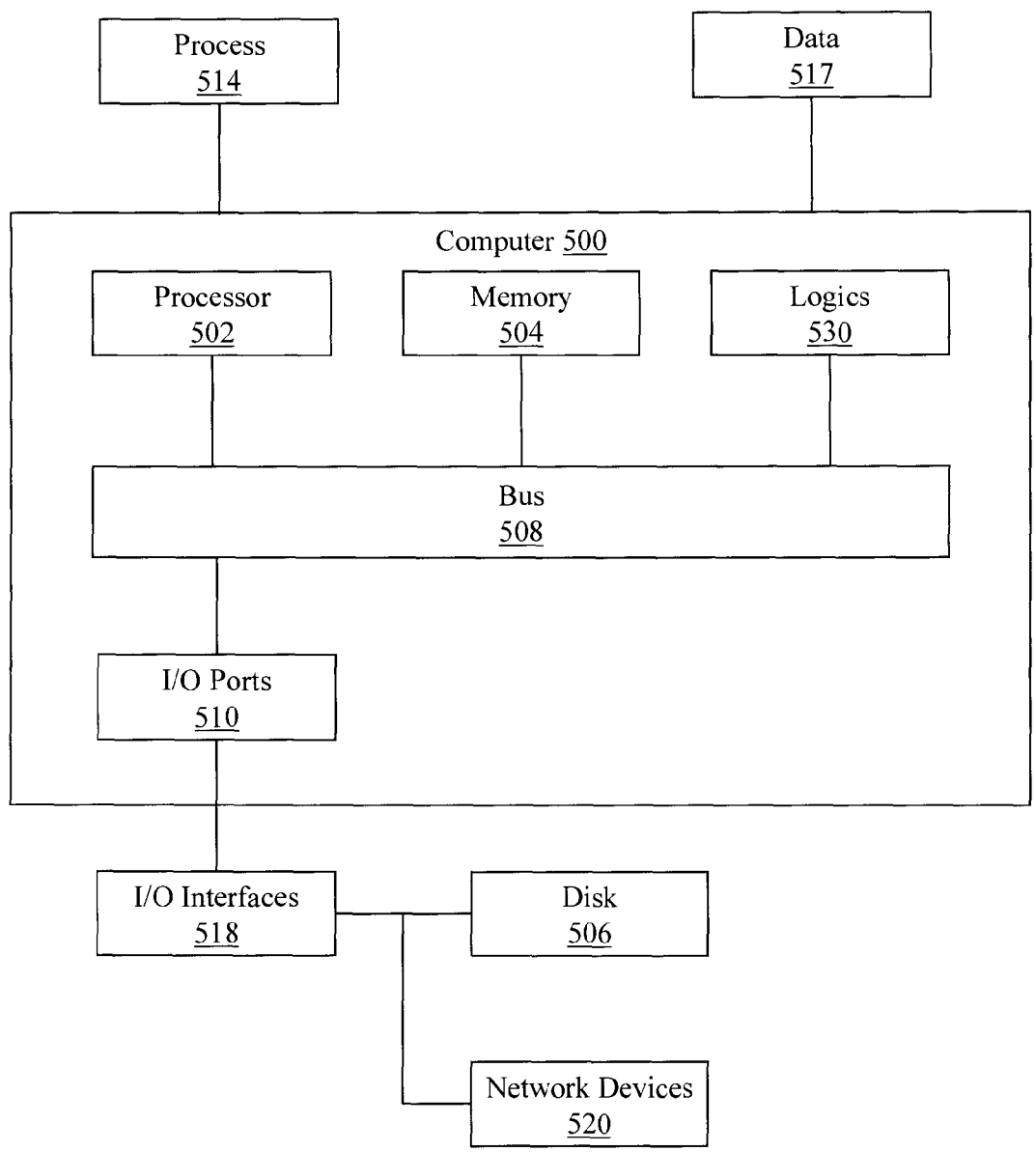
FIG. 5 illustrates an example computer in which example methods, apparatus, and ASICs described herein operate.

FIG. 5 illustrates an example computer 500 in which example methods illustrated herein can operate and in which example logics may be implemented. In different examples, computer 500 may be part of proteomic profiling system, an MRS system, an MRI system, may be operably connectable to an MRI system, may be operably connected to a radiologic imaging system, may be part of a digital whole slide scanner system, or may be part of a CADx system.

Computer 500 includes a processor 502, a memory 504, and input/output ports 510 operably connected by a bus 508. In one example, computer 500 may include a set of logics 530 that perform a method of automatically analyzing a cancerous prostate using GNCCA with a VIP score. Thus, the set of logics 530, whether implemented in computer 500 as hardware, firmware, software, and/or a combination thereof may provide means (e.g., hardware, software) for analyzing a cancerous prostate using GNCCA with a VIP score. In different examples, the set of logics 530 may be permanently and/or removably attached to computer 500. In one embodiment, the functionality associated with the set of logics 530 may be performed, at least in part, by hardware logic components including, but not limited to, field-programmable gate arrays (FPGAs), application specific integrated circuits (ASICs), application specific standard products (ASSPs), system on a chip systems (SOCs), or complex programmable logic devices (CPLDs). In one embodiment, individual members of the set of logics 530 are implemented as ASICs or SOCs.

Processor 502 can be a variety of various processors including dual microprocessor and other multi-processor architectures. Memory 504 can include volatile memory and/or non-volatile memory. A disk 506 may be operably connected to computer 500 via, for example, an input/output interface (e.g., card, device) 518 and an input/output port 510. Disk 506 may include, but is not limited to, devices like a magnetic disk drive, a tape drive, a Zip drive, a flash memory card, or a memory stick. Furthermore, disk 506 may include optical drives like a CD-ROM or a digital video ROM drive (DVD ROM). Memory 504 can store processes 514 or data 517, for example. Disk 506 or memory 504 can store an operating system that controls and allocates resources of computer 500.

Bus 508 can be a single internal bus interconnect architecture or other bus or mesh architectures. While a single bus is illustrated, it is to be appreciated that computer 500 may communicate with various devices, logics, and peripherals using other busses that are not illustrated (e.g., PCIE, SATA, Infiniband, 1394, USB, Ethernet).

Computer 500 may interact with input/output devices via I/O interfaces 518 and input/output ports 510. Input/output devices can include, but are not limited to, digital whole slide scanners, an optical microscope, a keyboard, a microphone, a pointing and selection device, cameras, video cards, displays, disk 506, network devices 520, or other devices. Input/output ports 510 can include but are not limited to, serial ports, parallel ports, or USB ports.

Computer 500 may operate in a network environment and thus may be connected to network devices 520 via I/O interfaces 518 or I/O ports 510. Through the network devices 520, computer 500 may interact with a network. Through the network, computer 500 may be logically connected to remote computers. The networks with which computer 500 may interact include, but are not limited to, a local area network (LAN), a wide area network (WAN), or other networks.

Figure 6:
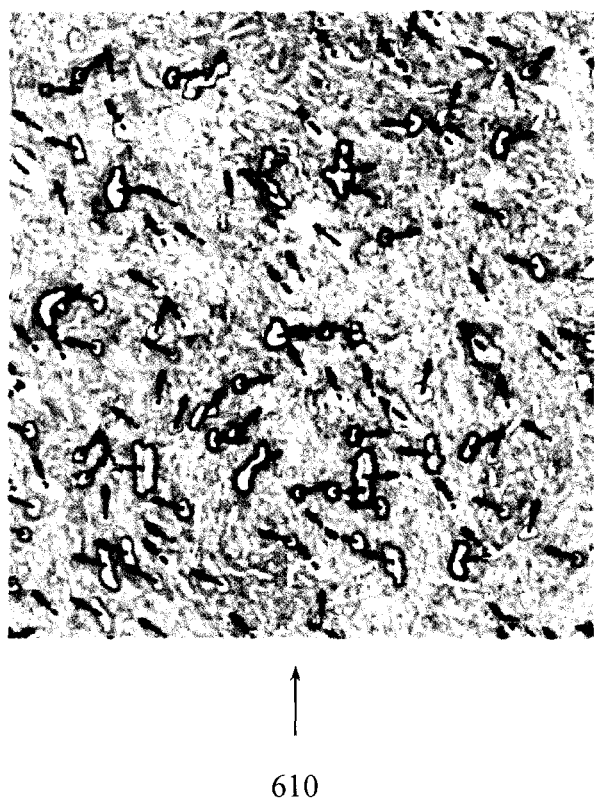
FIG. 6 illustrates example textural features extracted from an excised section of prostate.

FIG. 6 illustrates example textural features 610 extracted from an excised section of prostate. Textural features 610 may include cell nuclei, or clusters of cell nuclei.

Figure 7:
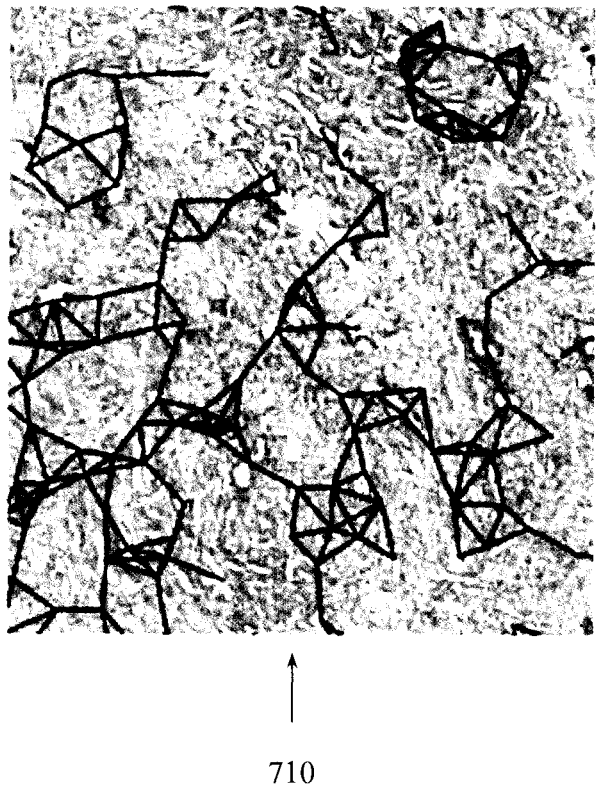
FIG. 7 illustrates example structural features extracted from an excised section of prostate.

FIG. 7 illustrates example structural features 710 extracted from an excised section of prostate. Structural features 710 may include cell graphs (CG), Voronoi graphs (VT), or Delaunay graphs (DT).

Figure 8:
FIG. 8 illustrates an example T2w MRI image.
Figure 8:

FIG. 8 illustrates an example T2w MRI image 810 of a section of prostate.

Figure 9:
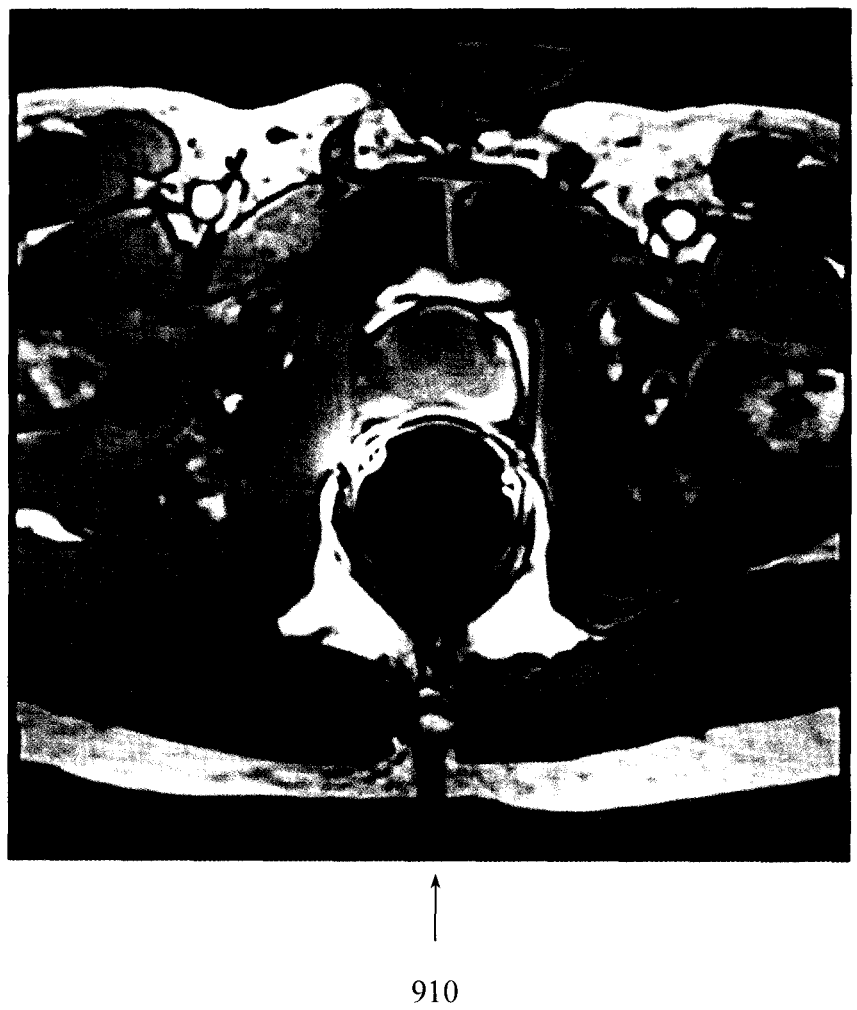
FIG. 9 illustrates an example DCE MRI image.

FIG. 9 illustrates an example DCE MRI image 910 of a section of prostate.

Figure 10:
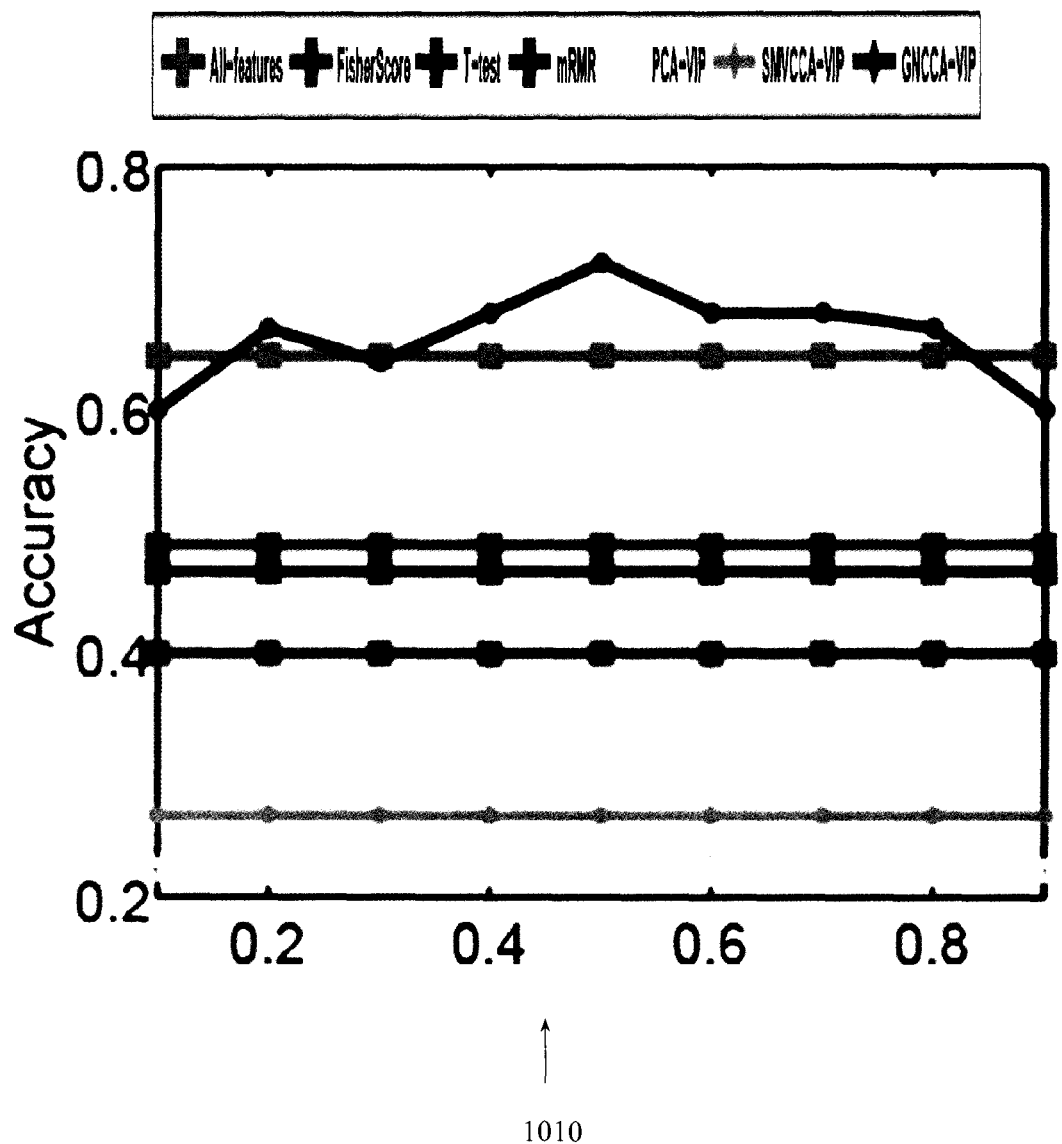
FIG. 10 is a graph illustrating the effect of varying a group sparsity controller on GNCCA accuracy in predicting CaP BcR.

FIG. 10 is a graph 1010 illustrating the effect of varying a group sparsity controller $\beta$ on GNCCA accuracy in predicting CaP BcR. In graph 1010, the group sparsity controller $\beta$ is varied from 0.1 to 0.9 while fixing r=1, $\sigma$=0.9, and M=1.

Figure 11:
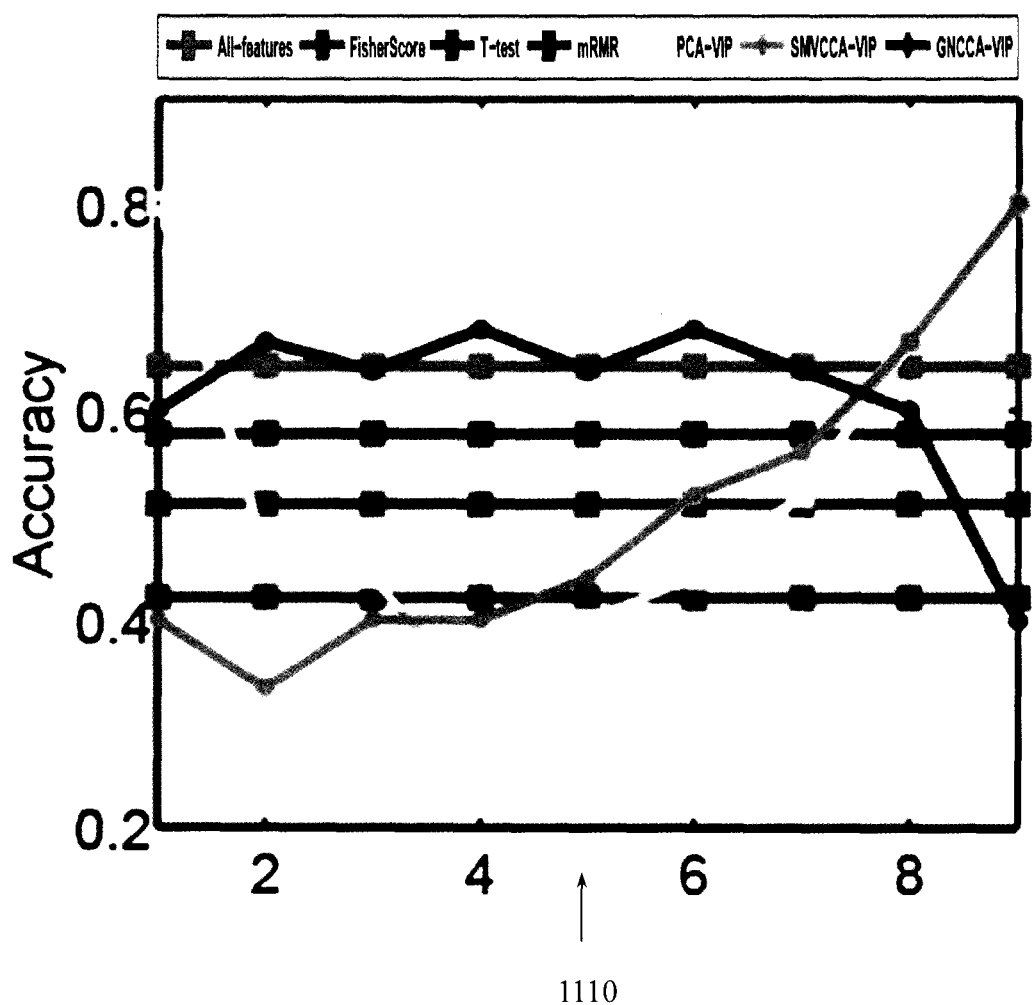
FIG. 11 illustrates a graph illustrating the effect of varying an intrinsic dimensionality on GNCCA accuracy in predicting CaP BcR.

FIG. 11 illustrates a graph 1110 illustrating the effect of varying an intrinsic dimensionality r on GNCCA accuracy in predicting CaP BcR. In graph 1110, the intrinsic dimensionality r is varied from 1 to 9 while fixing $\beta$=0.7, $\sigma$=0.9, and M=5.

Figure 12:
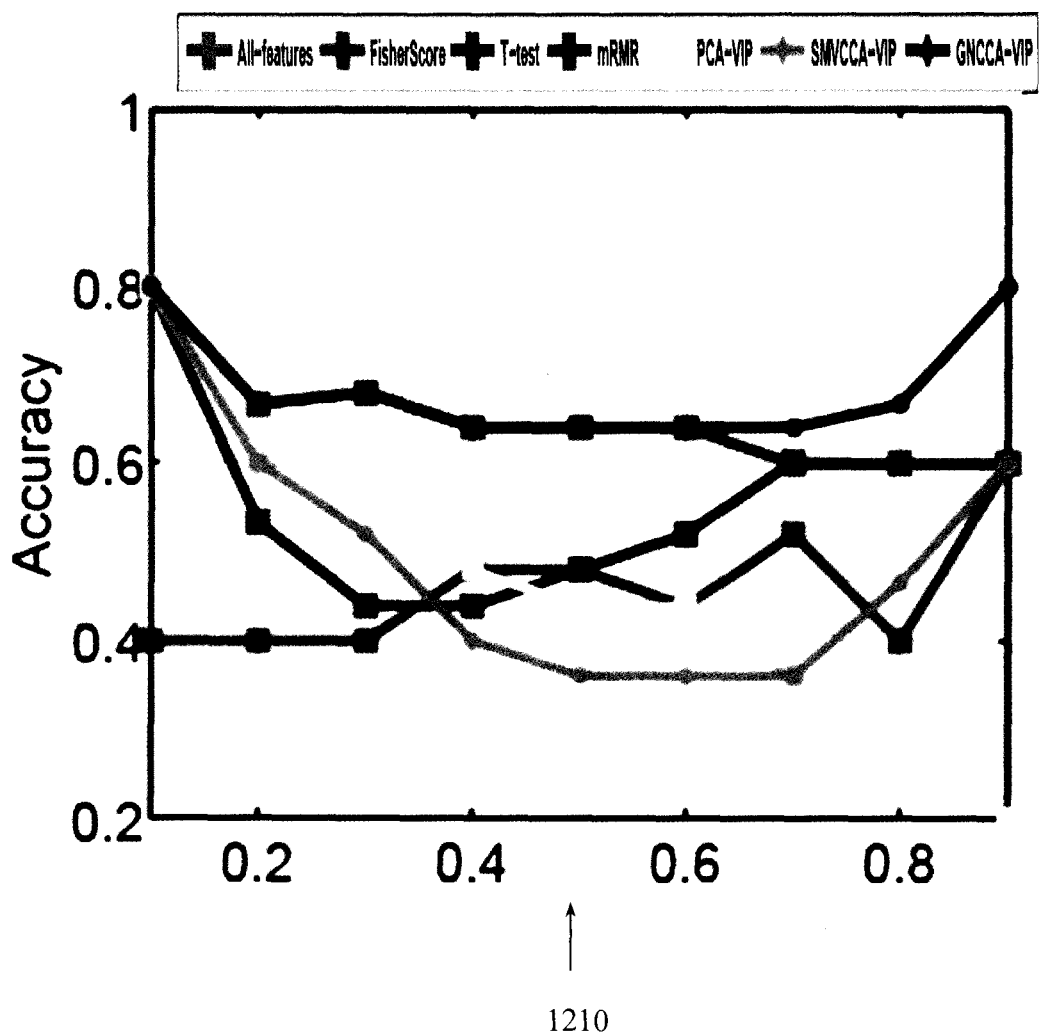
FIG. 12 illustrates a graph illustrating the effect of varying a controller that controls a threshold number of selected features on GNCCA accuracy in predicting CaP BcR.

FIG. 12 illustrates a graph 1210 illustrating the effect of varying a controller $\sigma$ that controls a threshold number of selected features on GNCCA accuracy in predicting CaP BcR. In graph 1210, the controller $\sigma$ is varied from 0.1 to 0.9 while fixing $\beta$=0.7, r=2, and M=1.

Figure 13:
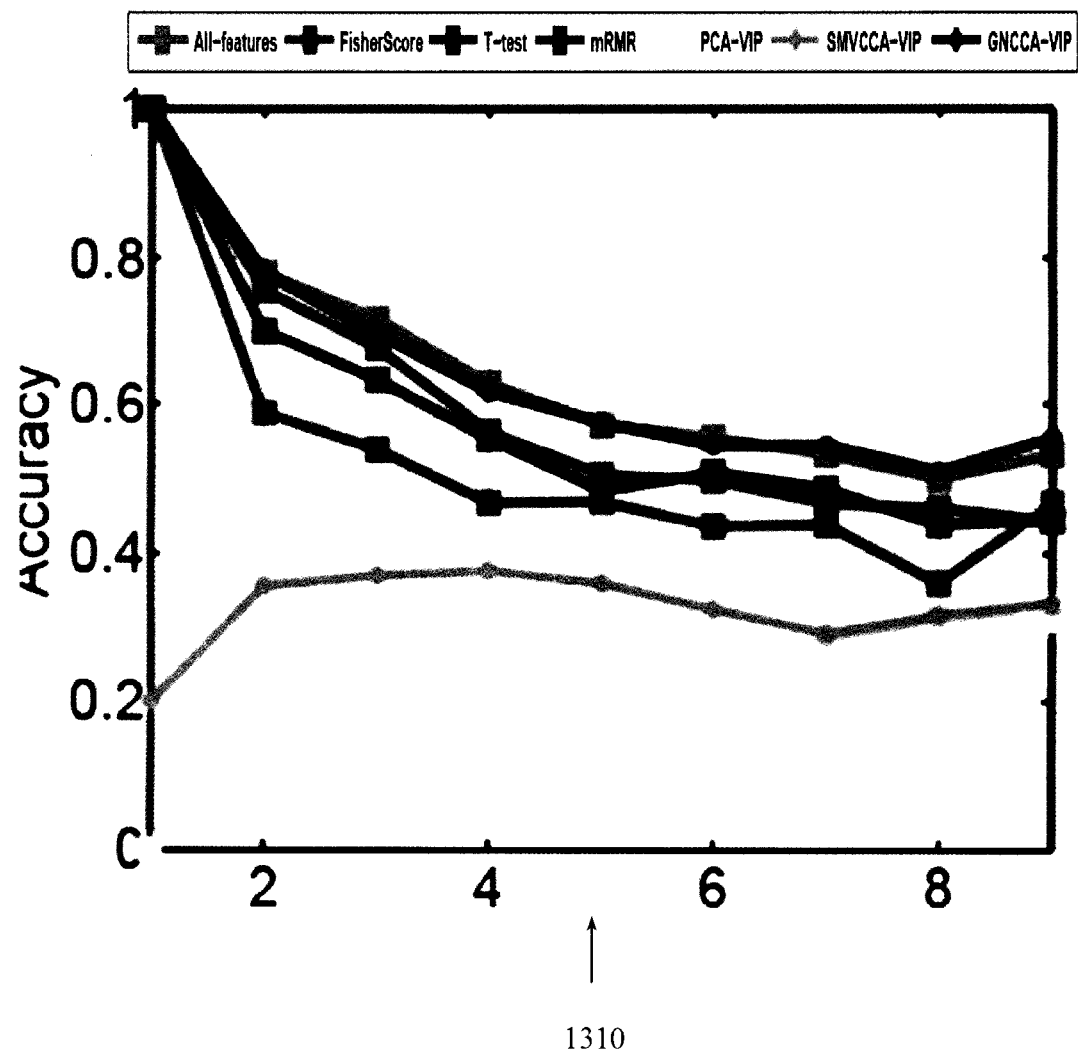
FIG. 13 illustrates a graph illustrating the effect of varying the number of patients used as testing samples on GNCCA accuracy in predicting CaP BcR.

FIG. 13 illustrates a graph 1310 illustrating the effect of varying the number of patients M used as testing samples on GNCCA accuracy in predicting CaP BcR. In graph 1310, the number of patients removed M is varied from 1 to 9 while fixing $\beta$=0.9, r=1, and $\sigma$=0.7.

References to "one embodiment", "an embodiment", "one example", and "an example" indicate that the embodiment(s) or example(s) so described may include a particular feature, structure, characteristic, property, element, or limitation, but that not every embodiment or example necessarily includes that particular feature, structure, characteristic, property, element or limitation. Furthermore, repeated use of the phrase "in one embodiment" does not necessarily refer to the same embodiment, though it may.

"Computer-readable storage medium", as used herein, refers to a medium that stores instructions or data. "Computer-readable storage medium" does not refer to propagated signals. A computer-readable storage medium may take forms, including, but not limited to, non-volatile media, and volatile media. Non-volatile media may include, for example, optical disks, magnetic disks, tapes, and other media. Volatile media may include, for example, semiconductor memories, dynamic memory, and other media. Common forms of a computer-readable storage medium may include, but are not limited to, a floppy disk, a flexible disk, a hard disk, a magnetic tape, other magnetic medium, an application specific integrated circuit (ASIC), a compact disk (CD), other optical medium, a random access memory (RAM), a read only memory (ROM), a memory chip or card, a memory stick, and other media from which a computer, a processor or other electronic device can read.

"Logic", as used herein, includes but is not limited to hardware, firmware, software in execution on a machine, or combinations of each to perform a function(s) or an action(s), or to cause a function or action from another logic, method, or system. Logic may include a software controlled microprocessor, a discrete logic (e.g., ASIC), an analog circuit, a digital circuit, a programmed logic device, a memory device containing instructions, and other physical devices. Logic may include one or more gates, combinations of gates, or other circuit components. Where multiple logical logics are described, it may be possible to incorporate the multiple logical logics into one physical logic. Similarly, where a single logical logic is described, it may be possible to distribute that single logical logic between multiple physical logics.

To the extent that the term "includes" or "including" is employed in the detailed description or the claims, it is intended to be inclusive in a manner similar to the term "comprising" as that term is interpreted when employed as a transitional word in a claim.

Throughout this specification and the claims that follow, unless the context requires otherwise, the words 'comprise' and 'include' and variations such as 'comprising' and 'including' will be understood to be terms of inclusion and not exclusion. For example, when such terms are used to refer to a stated integer or group of integers, such terms do not imply the exclusion of any other integer or group of integers.

To the extent that the term "or" is employed in the detailed description or claims (e.g., A or B) it is intended to mean "A or B or both". When the applicants intend to indicate "only A or B but not both" then the term "only A or B but not both" will be employed. Thus, use of the term "or" herein is the inclusive, and not the exclusive use. See, Bryan A. Garner, A Dictionary of Modern Legal Usage 624 (2d. Ed. 1995).

While example systems, methods, and other embodiments have been illustrated by describing examples, and while the examples have been described in considerable detail, it is not the intention of the applicants to restrict or in any way limit the scope of the appended claims to such detail. It is, of course, not possible to describe every conceivable combination of components or methodologies for purposes of describing the systems, methods, and other embodiments described herein. Therefore, the invention is not limited to the specific details, the representative apparatus, and illustrative examples shown and described. Thus, this application is intended to embrace alterations, modifications, and variations that fall within the scope of the appended claims.

What is claimed is:

1. A non-transitory computer-readable storage medium storing computer executable instructions that when executed by a computer control the computer to perform a method for automatically analyzing a cancerous prostate, the method comprising:

acquiring a set of data samples X and a set of labels Y associated with the set of data samples X from a plurality of feature views K, where the plurality of feature views K includes a first set of features acquired from a first modality, and a second set of features acquired from a second, different modality;

transforming trace($W^T C_{xy} W$) to the Frobenius-Norm $\|Z-WH\|_F^2$, where C is a covariance matrix of K,
$C_{xy}$ denotes the stacking of the covariance matrix C and $YY^T$,
$Z=[X^T Y^T]^T$,
H is a coefficient matrix, and
W is a basis matrix;

computing $$\min \frac{1}{2}\|Z - WH\|_F^2 + \alpha\|H\|_F^2 + \beta \sum_{k=1}^{K} \|W_k\|_{1,\infty},$$

$$\text{s.t. } \forall \|w_i^{(k)}\|^2 \leq 1-\beta, k=1,\ldots; i=1,\ldots r;$$

$$\forall \|w_i^{(y)}\|^2 = 1-\beta, i=1,\ldots r;$$

$$H \geq 0, W \geq 0,$$

where $W \in \mathcal{R}^{m \times r}$,
$H \in \mathcal{R}^{r \times n}$,
$\|H\|_F^2$ is a first penalty term that avoids an arbitrarily large H,
$\Sigma_{k=1}^{K}\|W_k\|_{1,\infty}$ is a second penalty term that constrains a group sparsity,
α controls the relative influence of the first penalty term $\|H\|_F^2$,
β controls the relative influence of the second penalty term,
K is the number of feature views,
r is a dimension of reduced representation, r<<m, and
$\| \|_{1,\infty}$ represents $l_{1,\infty}$-norm, where $l_{1,\infty}$-norm is defined by $\|W\|_{1,\infty} = \Sigma_{i=1}^{r}\|w_i\|_\infty = \|w_1\|_\infty + \ldots \|w_r\|_\infty$;

computing a Variable Importance in the Projections (VIP) score $\pi_j$ for a feature j, where j is a member of K;

selecting a reduced-dimensionality subset of features using a simultaneous between-view feature selection approach and within-view feature selection approach, based, at least in part, on the VIP score $\pi_j$ and a threshold σ, where the reduced-dimensionality subset of features is smaller than the first set of features and the second set of features;

controlling an automated prostate cancer (CaP) analysis system to predict a biochemical recurrence (BcR) or to predict a CaP grade, based, at least in part, on the selected reduced-dimensionality subset of features; and displaying the CaP grade or BcR score and the reduced-dimensionality subset of features on a computer monitor, a smartphone display, or a tablet display, where the first set of features is a set of histological features extracted from a hematoxylin and eosin (H&E) stained histology section of a section of CaP tissue, and the second set of features is a set of proteomic profiling values extracted from the H&E stained histology section, or where the first set of features is a set of textural features extracted from a T2 weighted magnetic resonance imaging (MRI) image of a section of CaP tissue, and the second set of features is a set of kinetic features extracted from a dynamic contrast-enhanced (DCE) MRI image of the section of CaP tissue, T2 being spin-spin relaxation.

2. The non-transitory computer-readable storage medium of claim 1, the method comprising optimizing $$\min \frac{1}{2}\|Z - WH\|_F^2 + \alpha\|H\|_F^2 + \beta \sum_{k=1}^{K} \|W_k\|_{1,\infty}$$

using a vector-block coordinate descent (BCD) approach.

3. The non-transitory computer-readable storage medium of claim 2, where optimizing $$\min \frac{1}{2}\|Z - WH\|_F^2 + \alpha\|H\|_F^2 + \beta\sum_{k=1}^{K}\|W_k\|_{1,\infty}$$

using a BCD approach includes:
fixing W;
updating a row vector $h_i \in \mathcal{R}^{1 \times n}$, i=1, ..., r as $$h_i \leftarrow \underset{h \geq 0}{\arg\min}\, \frac{1}{2}\|R_i - w_i h\|_F^2 + \alpha\|h\|_2^2, \text{ where}$$

$$R_i = Z - \sum_{j=1, j \neq i}^{r} w_j h_j;$$

fixing H and $W_{(y)}$;
updating a column vector $w_i^{(k)}$, k=1, ..., K as $$w_i^{(k)} \leftarrow \arg\underset{w \geq 0, \|w\|^2 \leq 1-\beta}{\min}\, \frac{1}{2}\|R_i^{(k)} - w^{(k)} h_i\|_F^2 + \beta\|w^{(k)}\|_\infty, \text{ where}$$

$$R_i^{(k)} = Z^{(k)} - \sum_{j=1, j \neq i}^{r} w_j^{(k)} h_j;$$

fixing $W_{1:K}$ and H; and
updating $W_{(y)}$ as $$w_i^{(y)} \leftarrow \arg\underset{w \geq 0, \|w\|^2 = 1-\beta}{\min}\, \frac{1}{2}\|R_i^{(y)} - w^{(y)} h_i\|_F^2, \text{ where}$$

$$R_i^{(y)} = Z^{(y)} - \sum_{j=1, j \neq i}^{r} w_j^{(y)} h_j.$$

4. The non-transitory computer-readable storage medium of claim 3, the method comprising solving $$h_i \leftarrow \underset{h \geq 0}{\arg\min}\, \frac{1}{2}\|R_i - w_i h\|_F^2 + \alpha\|h\|_2^2$$

in a closed form as $$h_i \leftarrow \left[\frac{w_i^T R_i}{2\alpha + \|w_i\|^2}\right]_+,$$

where [ ]$_+$ denotes an element-wise projection to non-negative numbers.

5. The non-transitory computer-readable storage medium of claim 2, the method comprising controlling a CaP voxel localizing system to localize CaP and non-CaP voxels, based, at least in part, on the selected feature.

6. The non-transitory computer-readable storage medium of claim 5, where the first set of features is a set of magnetic resonance spectroscopy (MRS) features extracted from a voxel of an MRS image of a section of CaP tissue, and the second set of features is a set of MRI features extracted from a voxel of an MRI image of the section of CaP tissue.

7. The non-transitory computer-readable storage medium of claim 1, the method comprising solving $$w_i^{(k)} \leftarrow \arg\underset{w \geq 0, \|w\|^2 \leq 1-\beta}{\min}\, \frac{1}{2}\|R_i^{(k)} - w^{(k)} h_i\|_F^2 + \beta\|w^{(k)}\|_\infty$$

by:
normalizing $w_i^{(k)*}$ s. t. $\|w_i^{(k)*}\|^2 \leq 1-\beta$; and
updating $w_i^{(k)*}$ as $$w_i^{(k)**} = \left[\frac{R_i^{(k)} h_i^{(T)}}{\|h_i\|^2}\right]_+ - w_i^{(k)*}.$$

8. The non-transitory computer-readable storage medium of claim 7, the method comprising solving $$w_i^{(y)} \leftarrow \arg\underset{w \geq 0, \|w\|^2 = 1-\beta}{\min}\, \frac{1}{2}\|R_i^{(y)} - w^{(y)} h_i\|_F^2$$

by:
updating w as $$w_i^{(y)} \leftarrow \left[\frac{R_i^{(y)} h_i^{(T)}}{\|h_i\|^2}\right]_+;$$

and
normalizing $w_i^{(y)}$ by computing $$w_i^{(y)} \leftarrow \frac{w_i^{(y)}}{\|w_i^{(y)}\|}\sqrt{1-\beta}.$$

9. The non-transitory computer-readable storage medium of claim 8, where computing the VIP score $\pi_j$ for the feature j includes computing $$\pi_j = \sqrt{\frac{m \sum_{i=1}^{r} \|w_y\|_2^i h_i h_i^T \left(\frac{w_{ji}}{\|w_i\|}\right)^2}{\sum_{i=1}^{r} \|w_y\|_2^i h_i h_i^T}},$$

where $$Z = \begin{bmatrix} X \\ Y \end{bmatrix} \approx \begin{bmatrix} W \\ W_y \end{bmatrix} H;$$

$X \approx WH$;
$Y^T \approx H^T W_y^T$; and
$w_y^i \in W_y$ is a column entry of $W_y$.

10. The non-transitory computer-readable storage medium of claim 9, where W is a reduced feature space, and where $X \approx WH$ introduces a lower feature representation H in W.

11. The non-transitory computer-readable storage medium of claim 10, where $Y^T \approx H^T W_y^T$ models the lower feature representation H regressing to class labels $Y^T$.

12. The non-transitory computer-readable storage medium of claim 11, where the threshold σ is defined as σ: 0<σ<1, and where σ automatically determines the number of selected features.

13. The non-transitory computer-readable storage medium of claim 12, where selecting a reduced-dimensionality subset of features based, at least in part, on the VIP score $\pi_j$ and the threshold σ includes selecting a feature with a VIP score $\pi_j$ greater than or equal to $\sigma \times \pi_{max}$, where $\pi_{max}$ is the largest VIP score.

14. The non-transitory computer-readable storage medium of claim 13, where β, r, and σ are determined using a Leave-M-Patient-out cross validation approach, where M varies according to a number of patients in a data set, and where $\alpha \|H\|_F^2$ is fixed at $0.1\|H\|_F^2$.

15. A non-transitory computer-readable storage medium storing computer executable instructions that when executed by a computer control the computer to perform a method for grading cancer or predicting cancer recurrence, the method comprising:

identifying a set of discriminative features from multiple feature views using group sparse non-negative supervised canonical correlation analysis (GNCCA);

ranking the set of discriminative features using a Variable Importance in the Projections (VIP) score;

selecting a reduced-dimensionality subset of discriminative features from the set of discriminative features based, at least in part, on the VIP score, where the reduced-dimensionality subset has a smaller size than the set of discriminative features, where the reduced-dimensionality subset of discriminative features includes at least one feature obtained from a first feature view, and at least one feature obtained from a second, different feature view, where the reduced-dimensionality subset of discriminative features is selected simultaneously using a between-view feature selection approach and a within-view feature selection approach, and where the reduced-dimensionality subset expresses an influence of the first feature view and the second feature view on the reduced-dimensionality subset; and providing a cancer grade based, at least in part, on the reduced dimensionality subset of discriminative features, or providing a cancer recurrence score based, at least in part, on the reduced dimensionality subset of discriminative features.

16. An application specific integrated circuit (ASIC) that generates a prognostic score or a diagnostic grade for a disease, where the ASIC includes gates configured to:

acquire a set of features from a plurality of modalities, where the plurality of modalities includes imaging modalities or non-imaging modalities;

identify a set of discriminative features from the plurality of modalities using group sparse non-negative supervised canonical correlation analysis (GNCCA);

rank the set of discriminative features using a Variable Importance in the Projections (VIP) score;

simultaneously select a reduced dimensionality subset of discriminative features from the set of discriminative features using a between-view feature selection approach and a within-view feature selection approach based, at least in part, on the VIP score, where the reduced dimensionality subset of discriminative features has a smaller size than the set of discriminative features, where the reduced dimensionality subset of discriminative features includes at least one feature obtained from a first modality, and at least one feature obtained from a second, different modality, where a feature unique to the first modality is simultaneously selectable with a feature common to the first modality and the second modality, and where the reduced-dimensionality subset expresses an influence of the discriminative features on the reduced-dimensionality subset; and provide a diagnostic grade or a prognostic score based, at least in part, on the reduced dimensionality subset of discriminative features.

\* \* \* \* \*